United States Patent [19]

Metz et al.

[11] 4,146,637
[45] Mar. 27, 1979

[54] ANTI-INFLAMMATORY N-ACYL SUBSTITUTED BENZAMIDES

[75] Inventors: Gunter Metz; Manfred Specker, both of Blaubeuren, Fed. Rep. of Germany

[73] Assignee: Ludwig Merckle K.G., Chem. Pharm. Fabrik, Blaubeuren, Fed. Rep. of Germany

[21] Appl. No.: 799,166

[22] Filed: May 23, 1977

[30] Foreign Application Priority Data

May 24, 1976 [DE] Fed. Rep. of Germany ....... 2623228

[51] Int. Cl.$^2$ .................. A61K 31/165; A61K 31/17; C07C 101/00; C07C 103/78
[52] U.S. Cl. ............................ 424/300; 260/559 S; 260/559 A; 260/559 B; 260/501.15; 260/553 A; 260/558 S; 260/558 A; 260/559 T; 424/263; 424/311; 424/322; 424/324; 546/291; 546/309; 546/316; 560/29; 560/252
[58] Field of Search ............. 560/29, 252; 260/559 S, 260/559 A, 559 B; 424/300, 311, 324

[56] References Cited

U.S. PATENT DOCUMENTS

| 3,818,021 | 6/1974 | Thuillier et al. | 260/559 A X |
| 3,898,278 | 8/1975 | Ghelardoni et al. | 260/559 S |
| 4,002,655 | 1/1977 | Hawkins | 260/559 S X |

Primary Examiner—Thomas Waltz
Attorney, Agent, or Firm—Roylance, Abrams, Berdo & Farley

[57] ABSTRACT

There are disclosed N-acyl substituted benzamides of the general formula:

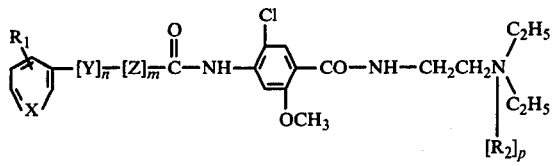

wherein:
X is carbon or nitrogen;
$R_1$ is hydrogen, alkyl, halogen, trifluoromethyl, alkoxy, phenoxy or acetoxy;
Y is the radical —O—, —NH— or —S—;
Z is an alkylene group containing 1 to 5 carbon atoms, or an alkenylene group containing 1 to 5 carbon atoms, either of which group may be unsubstituted or substituted by an alkyl, alkenyl, phenyl, cycloalkyl, acetyl, amino or halogenphenoxy group;
$R_2$ is hydrogen, an alkyl group containing 1 to 4 carbon atoms, an alkenyl group containing 1 to 4 carbon atoms in which either the alkyl or the alkenyl group may be unsubstituted or substituted with a halogen, phenyl or halogenphenyl substituent; and
the value of n, m, and p may each be 0 or 1, and in the case of p=1, pharmaceutically acceptable salts thereof.

Also disclosed is a method for making such compounds and pharmaceutical compositions containing such compounds.

5 Claims, No Drawings

ANTI-INFLAMMATORY N-ACYL SUBSTITUTED BENZAMIDES

This invention relates to new N-acyl substituted benzamides, to a process for their preparation and to the use of such compounds in a pharmaceutical composition.

The compound metoclopramide is a compound known in the art as an antiemetic. The preparation of this compound, which has the formula:

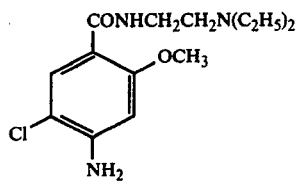

is described in U.S. Pat. No. 3,177,252. German Offenlegungsschriften Nos. 2,330,425 and 2,331,262 and German Auslegeschriften Nos. 1,518,271 and 1,518,310 further disclose the use of this compound as neuroleptic, psycholeptic, antiarrhytmic, analgesic, spasmolytic, choleretic, sedative, and antihistaminic agents. The acute toxicity of this compound is reported by German Offenlegungsschriften No. 2,330,425 to be as follows:

| $LD_{50}$ | oral | rat | 235 mg/kg |
|---|---|---|---|
| $LD_{50}$ | i.p. | rat | 180 mg/kg |
| $LD_{50}$ | i.p. | mouse | 242 mg/kg |

It is an object of this invention to provide compounds having desirable pharmacological characteristics and having a toxicity both orally (p.o.) as well as intraparitoneally (i.p.) lower than that of metoclopramide.

This, and other objects, are obtained by the practice of this invention which, briefly, comprises providing a new N-acyl substituted benzamide having the general formula (I):

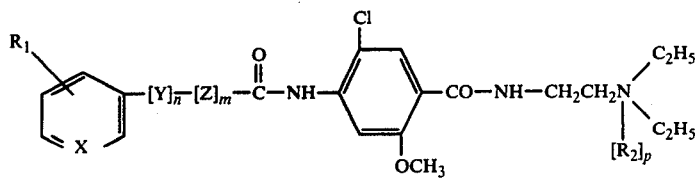

wherein:

X is carbon or nitrogen;

$R_1$ is hydrogen, alkyl, halogen, trifluoromethyl, alkoxy, phenoxy or acetoxy;

Y is the radical —O—, —NH— or —S—;

Z is an alkylene group containing 1 to 5 carbon atoms, or an alkenylene group containing 1 to 5 carbon atoms, either of which group may be unsubstituted or substituted by an alkyl, alkenyl, phenyl, cycloalkyl, acetyl, amino or halogenphenoxy group;

$R_2$ is hydrogen, an alkyl group containing 1 to 4 carbon atoms, an alkenyl group containing 1 to 4 carbon atoms in which either the alkyl or the alkenyl group may be unsubstituted or substituted with a halogen, phenyl or halogenphenyl substituent; and the value of n, m, and p may each be 0 or 1, and in the case of p = 1, pharmaceutically acceptable salts thereof.

When any of the above defined groups is halogen, it may be fluorine, chlorine, bromine or iodine and is preferably chlorine or fluorine. For the group $R_1$, the p- and o- position, especially the p- position is preferred. However, when $R_1$ is the trifluoromethyl group, it is preferably in the m- position.

When the group $R_1$ is an alkyl radical, it may be methyl, ethyl, propyl, isopropyl, n-butyl, t-butyl or n-pentyl, or a branched pentyl group. Preferably, the alkyl group contains from 1 to 3 carbon atoms. The methyl group is particularly preferred.

Examples of suitable straight chain or branched chain alkenylene groups are ethenylene, propenylene, butenylene, or pentenylene groups, always with a double bond.

Whenever $R_2$ is a halogenalkyl radical, it is preferably a methoiodide, an ethyliodide or a butylbromide radical.

The compounds of formula (I) are prepared in accordance with the practice of this invention by reacting a carboxylic acid of the general formula (II)

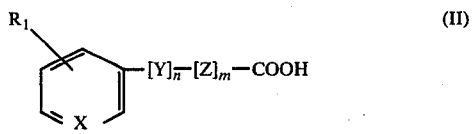

in which $R_1$, X, Y, Z, n, and m have the meanings previously defined with metoclopramide. The group $R_2$ may be introduced into the compound, i.e., the compound of (I), wherein p has a value of 1, in a manner known in the art for the purpose of producing a quaternary ammonium compound.

Suitable acid derivatives of compound (II), such as acid chlorides, acid anhydrides or esters, may be used in place of the free acid. The direct conversion of the carboxylic acid of formula (II) with metoclopramide preferably is accomplished in an aromatic solvent or a halogenated hydrocarbon while heating to reflux temperature. The conversion may also take place in the same manner in any other suitable inert solvent or even in a solvent-free system in the presence of a component which will split off water, such as, for example, phosphorous oxychloride, phosphorous trichloride, phosphorous pentachloride or dicyclohexylcarbodiimide. When a solvent is used, it is used in anhydrous form. The molar ratio between carboxylic acid of the formula (II) and metoclopramide in the reaction system preferably amounts to from 1:1 to 1:2. The basic acylamide obtained may be converted by reaction with a pharmaceutically acceptable acid into the corresponding salt or may be quaternized by reaction with a halogen alkane.

The following examples illustrate the preparation of the compounds of this invention:

EXAMPLE 1

Nicotinic acid (6.82 grams); (0.075 mole) and metoclopramide (14.9 grams; (0.95 mole) having the melting point of 148° C. are dissolved in 100 ml. of chloroform. At ambient temperature, 5.6 grams of phosphorous oxychloride are added drop by drop and the batch is heated for three more hours under reflux. After extraction with 80 ml. of 10% caustic soda solution, and subsequently with water, the chloroform solution is concentrated in a vacuum and the distillation residue having a boiling point of 100 to 140° C. is recrystallized from benzene. There is thus obtained 10.4 g. (51.4% of theory) of 4-nicotinoylamino-5-chloro-2-methyoxy-N-[2-(diethylamino)ethyl]benzamide having a melting point of 99° to 100° C.

EXAMPLE 2

The hydrochloride salt of the compound of Example 1 is prepared. The compound is recrystallized from a mixture of ethyl acetate and isopropanol and has a melting point of 213° to 214° C. It has IR peaks (KBr) at 3360, 3000, 1690 and 1644 $cm^{-1}$.

EXAMPLE 3

Metoclopramide (14.9 g.; 0.05 mole) is suspended in 100 ml. of xylene and after addition of 2-phenylbutyric acid anhydride (46.5 g.; 0.15 mole) having a melting point of 150° C./1.15 torr, the mixture is heated for three hours to 120° C. The mixture is extracted with diluted caustic soda solution and is then concentrated. The distillation residue is recrystallized from diisopropylether, resulting in 11.7 g. (56.2% of theory) of 4-(2-phenylbutyroylamino)-5-chloro-2-methoxy-N-[2-diethylaminoethyl]benzamide having a melting point of 118°-119° C.

IR(KBr): 3350, 3250, 1715, 1700, 1635 $cm^{-1}$.

EXAMPLE 4

The citrate of the product obtained in Example 3 is produced by esterification with citric acid. The product has a melting point of 69° C.

EXAMPLE 5

2-Phenyl-2-ethylbutyric acid (14.4 g.; 0.075 mole) and metoclopramide (14.9 g.; 0.05 mole) are suspended in 100 ml. of toluene. To this mixture is added 5.6 g. of phosphorous oxychloride drop by drop while heating slightly at 30°-40° C. After the addition is completed, it is heated for three hours under reflux. After extraction with 10% caustic soda solution and water, the organic phase is concentrated and the residue is recrystallized from gasoline (boiling point 100°-140° C.). There is thus obtained 12.2 g. of 4-(2-phenyl-2-ethylbutyroylamino)-5-chloro-2-methoxy-N-[2-(diethylamino)ethyl]benzamide (51.5% of theory) having a melting point of 113° C. IR(KBr): 3390, 1708, 1665 $cm^{-1}$.

EXAMPLE 6

Metoclopramide (59.8 g.; 0.2 mole) and triethylamine (30.0 g; 0.3 mole) are dissolved in 400 ml. of chloroform. To this mixture there is added dropwise 2-(4-chlorphenoxy)-2-methylpropionic acid chloride (72.0 g.; 0.3 mole). The mixture is heated under reflux for two hours and is subsequently mixed with 100 ml. of 20% caustic soda solution and with water. After evaporation, the distillation residue is recrystallized from methanol whereby 73.2 g. (73.7% of theory) of 4-[2-(4-chlorphenoxy)isobutyroylamino]-5-chloro-2-methoxy-N-[2-(diethylamino)-ethyl]benzamide having a melting point of 120°-121° C. is obtained.

IR(KBr): 3390, 1700, 1660 $cm^{-1}$.

Elementary analysis:

$CH_{24}H_{31}Cl_2N_3O_4$(496.4) calc.: C=58.07; H=6.30; N=8.46; Cl=14.29; found: C=58.20; H=6.39; N=8.52; Cl=14.49

EXAMPLE 7

The citrate of the compound of Example 6 is obtained by reaction with citric acid. This compound has a melting point of 142° C.

EXAMPLE 8

The tartrate of the product obtained in Example 6 is obtained by reaction with tartaric acid. The product has a melting point of 185° C.

EXAMPLE 9

The hydrochloride of the product of Example 6 is obtained by reaction with hydrochloric acid. The product has a melting point of 185° C.

EXAMPLE 10

The amide described in Example 5 (4.74 g.; 0.01 mole) is dissolved while heating slightly in 30 ml. of acetonitrile and the solution is mixed with methyliodide (1.42 g.; 0.01 mole). The mixture is heated for another two hours to 50° C. The crystallizate obtained is hydroextracted and is recrystallized from a small amount of absolute ethanol. There is thus obtained 4.7 g. (76.3% of yield theory) of 4-(2-phenyl-2-ethylbutyroylamino)-5-chloro-2-methoxy-N-[2-(diethylamino)ethyl]benzamide-methoiodide, having a melting point of 150° C.

EXAMPLE 11

The amide described in Example 6 (4.9 g.; 0.01 mole) and ethyliodide (1.56 g.; 0.01 mole) are heated for three hours under reflux in 30 ml. of acetone. After concentration, the distillation residue is recrystallized from ethyl acetate, whereby 5.1 g. (78.2% of theory) of 4-[2-(4-chlorophenoxy)isobutyroylamino]-5-chloro-2-methoxy-N-[2-(diethylamino)ethyl]benzamide-ethoiodide, having a melting point of 135°-136° C. are obtained.

Following the procedures described in Examples 1 and 10, more compounds were produced. The structures of these compounds are set forth in the accompanying table, along with the structures of Examples 1 to 11, by defining the various substituents on compound (I). It is understood that a dash in a column under a particular substituent indicates that that substituent is not present in that example. In those cases where p has a value of 1, i.e., where there is an $R_2$ group present, the acid group of the quartenary salt is listed in the next to the last column. The numbers in the column under $R_1$ indicate the position of the substituent on the ring.

TABLE I

| Ex. | X | $R_1$ | Y | Z | $R_2$ | Acid group (when p=1) | Melting Point |
|---|---|---|---|---|---|---|---|
| 1 | N | H | — | — | — | — | 99–100 |
| 2 | N | H | — | — | H | Cl | 213–214 |

TABLE I-continued

| Ex. | X | R₁ | Y | Z | R₂ | Acid group (when p=1) | Melting Point |
|---|---|---|---|---|---|---|---|
| 3 | C | H | — | —CH— \| C₂H₅ | — | — | 118–119 |
| 4 | C | H | — | —CH— \| C₂H₅ | H | citrate | 69 |
| 5 | C | H | — | C₂H₅ \| —C— \| C₂H₅ | — | — | 113 |
| 6 | C | 4-Cl | 0 | CH₃ \| —C— \| CH₃ | — | — | 120–121 |
| 7 | C | 4-Cl | 0 | CH₃ \| —C— \| CH₃ | H | citrate | 142 |
| 8 | C | 4-Cl | 0 | CH₃ \| —C— \| CH₃ | H | tartrate | 185 |
| 9 | C | 4-Cl | 0 | CH₃ \| —C— \| CH₃ | H | Cl | 185 |
| 10 | C | H | — | C₂H₅ \| —C— \| C₂H₅ | CH₃ | I | 150 |
| 11 | C | 4-Cl | 0 | CH₃ \| —C— \| CH₃ | C₂H₅ | I | 135–136 |
| 12 | C | H | — | — | — | — | 113–114 |
| 13 | C | H | — | — | H | Cl | 206 |
| 14 | C | 3,4,5-OCH₃ | — | — | — | — | 132 |
| 15 | C | 3,4,5-OCH₃ | — | — | H | Cl | 213 |
| 16 | C | 3,4,5-OCH₃ | — | — | CH₃ | I | 169 |
| 17 | C | 4-Cl | — | — | — | — | 144–146 |
| 18 | C | 4-Cl | — | — | CH₃ | I | 241 |
| 19 | C | 2-OC₆H₅ | — | — | — | — | 136–137 |
| 20 | C | 2-OC₆H₅ | — | — | H | Cl | 214 |
| 21 | C | 2-OCOCH₃ | — | — | — | — | 81–82 |
| 22 | C | 2-OCOCH₃ | — | — | CH₃ | I | 134–135 |
| 23 | C | H | — | —CH₂— | — | — | 100 |
| 24 | C | H | — | —CH₂— | CH₃ | I | 127 |
| 25 | C | H | — | —CH₂CH₂CH₂— | — | — | 64 |
| 26 | C | H | — | —CH— \| CH₃ | — | — | 69–70 |
| 27 | C | H | — | —CH— \| C₂H₅ | CH₃ | I | 131 |
| 28 | C | H | — | —CH— \| C₆H₅ | — | — | 146–147 |
| 29 | C | H | — | —CH— \| C₆H₅ | H | citrate | 87 |
| 30 | C | H | — | —CH— \| C₆H₅ | CH₃ | I | 212 |
| 31 | C | H | — | —CH— \| C₆H₁₁ (=Cyclohexyl) | — | — | 130 |
| 32 | C | H | — | —CH— \| C₆H₁₁ | CH₃ | I | 244 |

TABLE I-continued

| Ex. | X | R$_1$ | Y | Z | R$_2$ | Acid group (when p=1) | Melting Point |
|---|---|---|---|---|---|---|---|
| 33 | C | H | — | —CHCH$_2$—<br>\|<br>COCH$_3$ | — | — | — |
| 34 | C | H | — | —CHCH$_2$—<br>\|<br>COCH$_3$ | CH$_3$ | I | 99–110 |
| 35 | C | H | — | —CH—<br>\|<br>NH$_2$ | — | — | 109 |
| 36 | C | H | — | —CH=CH— | — | — | 124–125 |
| 37 | C | H | — | —CH=CH— | H | Cl | 221 |
| 38 | C | H | — | —CH=CH— | CH$_3$ | I | 218–219 |
| 39 | C | H | — | —CH—<br>\|<br>CH$_2$ | — | — | 120 |
| 40 | C | 4-Cl | 0 | —CH$_2$— | — | — | 171 |
| 41 | C | 4-Cl | 0 | —CH$_2$— | H | citrate | 172 |
| 42 | C | 4-Cl | 0 | —CH$_2$— | H | tartrate | 163 |
| 43 | C | 4-Cl | 0 | —CH$_2$— | H | Cl | 223 |
| 44 | C | 4-Cl | 0 | —CH$_2$— | CH$_3$ | I | 242 |
| 45 | C | 4-Cl | 0 | —CH—<br>\|<br>CH$_3$ | — | — | 151 |
| 46 | C | 4-Cl | 0 | —CH—<br>\|<br>CH$_3$ | H | citrate | 105 |
| 47 | C | 4-Cl | 0 | —CH—<br>\|<br>CH$_3$ | H | tartrate | 198 |
| 48 | C | 4-Cl | 0 | —CH—<br>\|<br>CH$_3$ | H | Cl | 187 |
| 49 | C | 4-Cl | 0 | —CH—<br>\|<br>CH$_3$ | CH$_3$ | I | 175 |
| 50 | C | 4-Cl | 0 | CH$_3$<br>\|<br>—C—<br>\|<br>CH$_3$ | CH$_3$ | I | 169–170 |
| 51 | C | 2-Cl | 0 | —CH$_2$— | — | — | 165–166 |
| 52 | C | 2-Cl | 0 | —CH$_2$— | H | Cl | 216 |
| 53 | C | 3-CF$_3$ | 0 | —CH$_2$— | — | — | 160–161 |
| 54 | C | 3-CF$_3$ | 0 | —CH$_2$— | H | Cl | 225 |
| 55 | C | 4-Br | 0 | —CH$_2$— | — | — | 175 |
| 56 | C | 4-Br | 0 | —CH$_2$— | H | Cl | 231 |
| 57 | C | 4-Br | 0 | —CH$_2$— | H | maleinate | 171 |
| 58 | C | 4-Br | 0 | —CH$_2$— | H | fumarate | 189 |
| 59 | C | 4-F | 0 | —CH—<br>\|<br>OC$_6$H$_4$-4F | — | — | 103 |
| 60 | C | 4-F | 0 | —CH—<br>\|<br>OC$_6$H$_4$-4F | H | citrate | 80 |
| 61 | C | 4-I | 0 | —CH$_2$— | — | — | 175 |
| 62 | C | 4-I | 0 | —CH$_2$— | H | Cl | 238 |
| 63 | C | 4-Cl | 0 | —CH—<br>\|<br>OC$_6$H$_4$-4Cl | — | — | 104 |
| 64 | C | 4-CH$_3$ | 0 | —CH$_2$— | — | — | 154 |
| 65 | C | 4-CH$_3$ | 0 | —CH$_2$— | H | Cl | 225 |
| 66 | C | 4-CH$_3$ | 0 | —CH$_2$— | CH$_3$ | I | 227 |
| 67 | C | 4-Br | 0 | —CH—<br>\|<br>C$_6$H$_5$ | — | — | 132 |
| 68 | C | H | 0 | —CH$_2$— | — | — | 142 |
| 69 | C | H | NH | —CH$_2$— | — | — | 130 |
| 70 | C | H | S | —CH$_2$— | — | — | 111 |
| 71 | C | 4-CH$_3$ | 0 | —CH$_2$— | CH$_3$CH$_2$CH$_2$CH$_2$— | Br | 180 |
| 72 | C | H | — | —CH—<br>\|<br>CH$_2$ | CH$_3$CH$_2$CH$_2$CH$_2$— | Br | 142 |
| 73 | N | H | — | — | CH$_3$ | I | 155 |
| 74 | C | 4-Cl | 0 | CH$_3$<br>\|<br>—C—<br>\|<br>CH$_3$ | CH$_3$ | NO$_3$ | 122 |

TABLE I-continued

| Ex. | X | R₁ | Y | Z | R₂ | Acid group (when p=1) | Melting Point |
|---|---|---|---|---|---|---|---|
| 75 | C | 4-Cl | 0 | CH₃<br>—C—<br>CH₃ | CH₃ | OCOCH₃ | 71 |
| 76 | C | 4-Cl | 0 | CH₃<br>—C—<br>CH₃ | CH₃ | Cl | 147 |

An elemental analysis was conducted on several of the compounds obtained in the preceding examples. The results are set forth in Table II.

TABLE II

| | Elemental Analysis | | | | | |
|---|---|---|---|---|---|---|
| | Calculated | | | Found | | |
| Example | C | H | N | C | H | N |
| 1 | 59.33 | 6.22 | 13.83 | 59.31 | 6.09 | 13.73 |
| 5 | 65.87 | 7.65 | 8.86 | 64.91 | 7.48 | 8.64 |
| 11 | 47.79 | 5.70 | 6.43 | 46.54 | 5.56 | 6.50 |
| 14 | 47.21 | 5.54 | 6.60 | 46.76 | 5.71 | 6.58 |
| 21 | 59.67 | 6.31 | 9.07 | 59.07 | 6.21 | 9.45 |
| 23 | 63.22 | 6.75 | 10.05 | 63.15 | 6.72 | 10.20 |
| 31 | 67.38 | 7.47 | 8.41 | 66.88 | 7.65 | 8.47 |
| 35 | 61.17 | 6.53 | 12.97 | 60.41 | 6.80 | 12.81 |
| 36 | 64.25 | 6.56 | 9.77 | 63.81 | 6.43 | 9.61 |
| 39 | 64.25 | 6.56 | 9.77 | 63.89 | 6.46 | 9.91 |
| 40 | 56.41 | 5.81 | 8.97 | 56.26 | 5.80 | 8.98 |
| 45 | 57.27 | 6.06 | 8.71 | 57.46 | 6.14 | 8.67 |
| 69 | 61.03 | 6.75 | 12.94 | 62.12 | 6.60 | 12.21 |

The compounds of this invention have considerably less toxicity than metoclopramide. The toxicity of the compounds of Examples 9, 43 and 48 in the form of their hydrochlorides was determined and compared with the toxicity of metoclopramide dihydrochloride. The tests were conducted in mice, both p.o. and i.p. The results are set forth in Table 3.

TABLE III

| Compound | Doses mg/kg | Mode | Toxicity | Symptoms |
|---|---|---|---|---|
| metoclopromide (2HCl) | 300 | p.o. | LD 100 | — |
| | 200 | p.o. | — | relaxation of muscles, respiratory paralysis, lacrimation |
| | 100 | i.p. | — | respiratory paralysis |
| Example 9 (HCl) | 300 | p.o. | LD 0 | — |
| | 100 | i.p. | — | mild muscle relaxation |
| Example 43 (HCl) | 300 | p.o. | LD 0 | — |
| | 200 | p.o. | — | mild cramps and muscle relaxation |
| | 100 | i.p. | — | mild muscle relaxation, ataxia |
| Example 48 (HCl) | 300 | p.o. | LD 0 | — |
| | 200 | p.o. | — | mild cramps and muscle relaxation |
| | 100 | i.p. | — | mild lacrimation, slight muscle relaxation |

As the results of Table 3 show, the compounds of this invention have both lower toxicity and different side effects than metoclopramide. Compounds of this invention have interesting pharmacological characteristics. The pharmaco dynamics of the compounds prepared in Examples 9, 43 and 48 in the form of their hydrochlorides, as well as the reference compound, metoclopramide dihydrochloride, were determined by pharmacological screening for 54 group activities. The activities which were found were confirmed by secondary tests. The results of these comparative tests are summarized in Table IV. Additionally, the $ED_{100}$ of known group-specific comparative compounds is given.

TABLE 4

| Test Parameter | Animal[1] | Dose mg/kg | Mode of Admin. | Metoclopramide 2 HCL | Ex. 9 | Ex. 43 | Ex. 48 | Reference Compound mg/kg (=$ED_{100}$) |
|---|---|---|---|---|---|---|---|---|
| β-adrenergic blockage | r | $10^2$ | in vit. | — | $10^2$ MEC[3] | — | — | $1^2$ propanolol |
| Muscle relaxant | m | 300 | p.o. | 100 MED[4] | — | 300 MED | — | 100 phenobarbital |
| Amphetamine stereotype | m | 25 | p.o. | 25 MED | — | — | — | 5 chlorpromazin |
| Antiarrhytmice | m | 100 | i.p. | 100 MED | — | — | — | 100 guanidine |
| Antiedematous | r | 100 | p.o. | 50 MED | — | 100 MED | — | 50 phenybutazone |
| Cataleptic | m | 100 | p.o. | 100 MED | — | 100 MED | — | 100 phenobarbital |
| Antiaggressive | m | 50 | p.o. | 50 | — | — | — | 5 chlorpromazine |
| Anti-electroshock | m | 100 | p.o. | 100 MED | — | — | — | 10 diphenylhydomtoin |
| Blood flake aggregate stoppage | R | $10^2$ | in vit. | — | — | $5^2$ MEC | $5^2$ MEC | $5^2$ acetylsalicylic acid |
| Blood flake aggregate stoppage (ADP) | R | $100^2$ | in vit. | — | $50^2$ MEC | $10^2$ MEC | $10^2$ MEC | $100^2$ adenosine |
| Antiasthmatic | r | 100 | p.o. | — | — | 100 MED | 100 MED | 60 chromoglycinesodium |
| Antithrombotic | r | 100 | p.o. | — | — | 50 MED | 100 MED | 100 acetylsalicylic acid |
| Systematic | | | | | | | | 50 phenyl- |

TABLE 4-continued

| Test Parameter | Animal[1] | Dose mg/kg | Mode of Admin. | Metoclopramide 2 HCL | Ex. 9 | Ex. 43 | Ex. 48 | Reference Compound mg/kg (=ED$_{100}$) |
|---|---|---|---|---|---|---|---|---|
| anaphylactic | m | 100 | p.o. | — | — | 100 MED | — | toloxamine |
| Adjuvans arthritis stoppage | r | 100 | p.o. | — | — | 43%/46%[6] | 45%/33%[6] | |
| Intestinal relaxation | p | 1[2] | in vit. | — | 2[2] MEC | — | — | 1[2] papaverine |
| S. Aureus | | 20[2] | in vit. | — | 20[2] MIC[5] | 20[2] MIC | — | 0.06[2] ampicillin |
| E. Coli | | 20[2] | in vit. | — | 20[2] MIC | 20[2]MIC | 20[2] MIC | 0.5[2] ampicillin |

[1] m = mouse; r = rat; p = guinea pig; R = rabbit
[2] doses in mg/kg
[3] average effective concentration
[4] average minimal effective dose
[5] minimal inhibitory concentration
[6] Percent inhibition of the secondary lesions on the 14th day As the test results show, the compounds of this invention have special pharmacological characteristics as compared to metoclopramide. Thus, the compounds of Examples 40 and 45 exhibit very strong anti-inflammatory activity in the adjuvenous arthritis test and in the acute carrageneen experiment. This principle effectiveness is supplemented by weak antimicrobial as well as by antiallergic characteristics.

The compounds of this invention are, therefore, valuable therapeutic agents for the treatment of diseases involving inflammation and allergic symptoms, especially of a rheumatic and arthritic nature. Beyond that, they may also be used for diseases of the gastrointestinal tract.

The drugs of this invention are preferably administered orally, for example, in the form of tablets, capsules or liquids. They may be administered along with well known pharmaceutical adjuvants, e.g., lactose, starch, talcum and/or magnesium stearate.

The compounds of this invention may be administered in various doses, depending upon the disease being treated. For example, they may be administered in oral or rectal daily doses of 50 to 500 mg., preferably 100-200 mg., or in parenteral daily doses of 30-150 mg., preferably 50-100 mg. They may be administered in customary pharmaceutical forms.

The following examples illustrate various pharmaceutical formulations of the compounds of this invention:

EXAMPLE 77

| Tablets | |
|---|---|
| Active substance as in Example 43 (hydrochloride) | 15 mg. |
| micro-fine cellulose | 8 mg. |
| lactose | 8 mg. |
| potato starch | 9 mg. |
| talcum | 1.4 mg. |

EXAMPLE 78

| Soft Gelatine Capsules | |
|---|---|
| Active substance as in Example 10 | 50 mg. |
| wax | 4 mg. |
| soy lecithin | 2 mg. |
| partially hydrated vegetable oils | 2 mg. |
| Composition of the Capsule Envelope | |
| gelatin | 110 mg. |
| glycerin | 25 mg. |
| sorbitol | 47 mg. |
| ethyl and propylparabenes, dye | |

EXAMPLE 79

| Suppositories | |
|---|---|
| Active substance as in Example 46 (citrate) | 30 mg. |
| semisynthetic partial glyceride | 1.0 g. |

EXAMPLE 80

| Liquid | |
|---|---|
| Active substance as in Example 9 | 3.0 g. |
| invert sugar syrup | 25.0 g. |
| aroma | 0.5 g. |
| water | 100.0 ml. |

EXAMPLE 81

| Ampule Solution | |
|---|---|
| Active substance as in Example 2 | 20.0 mg. |
| benzylalcohol | 0.5 mg. |
| propyleneglycol | 0.1 ml. |
| water | ad. 1.0 ml. |

We claim:

1. N-acyl substituted benzamides of the general formula:

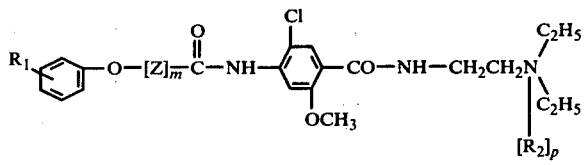

wherein:
R$_1$ is hydrogen, alkyl, halogen, trifluoromethyl, alkoxy, phenoxy or acetoxy;
Z is an alkylene group containing 1 to 5 carbon atoms, or an alkenylene group containing 1 to 5 carbon atoms, either of which group may be unsubstituted or substituted by an alkyl, alkenyl, phenyl, cycloalkyl, acetyl, amino or halogenphenoxy group;
R$_2$ is hydrogen, an alkyl group containing 1 to 4 carbon atoms, an alkenyl group containing 1 to 4 carbon atoms in which either the alkyl or the alkenyl group may be unsubstituted or substituted with a halogen, phenyl or halogenphenyl substituent; and the value of m and p may each be 0 or 1, and in the case of p = 1, pharmaceutically acceptable salts thereof.

2. A compound as defined in claim 1 wherein $R_1$ is 4-Cl, Z is the group —C(CH$_3$)$_2$—, $R_2$ is hydrogen and the values of m and p are each 1.

3. A compound as defined in claim 1 wherein $R_1$ is 4-Cl, Z is the radical —CH$_2$—, $R_2$ is hydrogen and the values of m and p are each 1.

4. A compound as defined in claim 1 wherein $R_1$ is 4-Cl, Z is the group

$R_2$ is hydrogen and the values of m and p are each 1.

5. A pharmaceutical composition having anti-inflammatory and anti-allergic activity comprising an effective anti-inflammatory and anti-allergic amount of a compound as defined in claim 1 and a pharmaceutically acceptable carrier therefor.

* * * * *